United States Patent
Li et al.

(10) Patent No.: US 12,195,553 B2
(45) Date of Patent: Jan. 14, 2025

(54) DEVELOPMENT OF RECOMBINANT CHICKEN IgY MONOCLONAL ANTIBODY AND scFv ANTIBODIES RAISED AGAINST HUMAN TYMIDINE KINASE 1 EXPRESSED IN MAMMALIAN CELLS AND USE THEREOF

(71) Applicant: SINO-SWED TONGKANG BIO-TECH (SHENZHEN) LIMITED, Guangdong (CN)

(72) Inventors: Zuosheng Li, Guangdong (CN); Hu Chen, Guangdong (CN); Huijun Li, Guangdong (CN); Li Dang, Guangdong (CN); Liwen Liang, Guangdong (CN); Cong Fang, Guangdong (CN); Junye Tan, Guangdong (CN); Ellen He, Guangdong (CN); Sven Isac Skog, Guangdong (CN); Ji Zhou, Guangdong (CN)

(73) Assignee: SINO-SWED TONGKANG BIO-TECH (SHENZHEN) LIMITED, Shenzhen (CN)

( * ) Notice: Subject to any disclaimer, the term of this patent is extended or adjusted under 35 U.S.C. 154(b) by 987 days.

(21) Appl. No.: 17/191,710

(22) Filed: Mar. 4, 2021

(65) Prior Publication Data

US 2021/0277147 A1    Sep. 9, 2021

Related U.S. Application Data

(63) Continuation of application No. PCT/CN2019/102619, filed on Aug. 26, 2019.

(30) Foreign Application Priority Data

Sep. 4, 2018 (CN) .......................... 201811026810.9

(51) Int. Cl.
    C07K 16/40   (2006.01)
    A61K 47/68   (2017.01)
    G01N 33/569  (2006.01)
    G01N 33/573  (2006.01)

(52) U.S. Cl.
    CPC .......... *C07K 16/40* (2013.01); *A61K 47/6871* (2017.08); *G01N 33/569* (2013.01); *G01N 33/573* (2013.01); *C07K 2317/23* (2013.01); *C07K 2317/622* (2013.01); *C07K 2319/02* (2013.01); *C07K 2319/40* (2013.01); *G01N 2333/9122* (2013.01); *G01N 2800/7023* (2013.01)

(58) Field of Classification Search
    CPC ................ C07K 16/40; C07K 2317/23; C07K 2317/622; C07K 2319/02; C07K 2319/40; A61K 47/6871; G01N 33/569; G01N 33/573; G01N 2333/9122; G01N 2800/7023
    See application file for complete search history.

(56) References Cited

U.S. PATENT DOCUMENTS

| | | | |
|---|---|---|---|
| 2010/0150939 A1 | 6/2010 | Blanchetot et al. | |
| 2012/0237530 A1 | 9/2012 | Matsuda et al. | |
| 2016/0311927 A1 | 10/2016 | Eriksson | |
| 2019/0070276 A1 | 3/2019 | O'Neill et al. | |
| 2020/0123243 A1 * | 4/2020 | Kim .................. | C07K 16/24 |

FOREIGN PATENT DOCUMENTS

| | | | | |
|---|---|---|---|---|
| CN | 1414017 A | 4/2003 | | |
| CN | 101027085 A | 8/2007 | | |
| CN | 101186922 A | 5/2008 | | |
| CN | 102432683 A | 5/2012 | | |
| CN | 102504027 A | 6/2012 | | |
| CN | 103304663 A | 9/2013 | | |
| CN | 105821010 A | 8/2016 | | |
| CN | 105980407 A | 9/2016 | | |
| EP | 2832368 A1 | 2/2015 | | |
| WO | WO-2015186721 A1 * | 12/2015 | ............. | C07K 16/10 |
| WO | 2017025944 A2 | 2/2017 | | |

OTHER PUBLICATIONS

Winkler et al. 2000. Journal of Immunology 165(8): 4505-4514. (Year: 2000).*
Edwards et al. 2003. Journal of Molecular Biology 334(1):103-118. (Year: 2003).*
Lloyd et al. 2009. Protein Engineering, Design and Selection 22(3): 159-168. (Year: 2009).*
Schroeder and Cavacini. 2010. Journal of Allergy and Clinical Immunology 125(2, Suppl.2): S41-S52. (Year: 2010).*
Sela-Culang et al. 2013. Frontiers in Immunology 4: 302. (Year: 2013).*

(Continued)

*Primary Examiner* — Brad Duffy
*Assistant Examiner* — Elizabeth A Shupe (57) ABSTRACT

Disclosed are the development of a recombinant chicken IgY monoclonal antibody and a recombinant chicken IgY single-chain variable fragment (scFv) antibody raised against human thymidine kinase 1 in mammalian cells and a preparation method and use thereof. A light chain of the scFv antibody includes an amino acid sequence shown in SEQ ID NO: 1, and a heavy chain of the scFv antibody includes an amino acid sequence shown in SEQ ID NO: 2.

17 Claims, 3 Drawing Sheets
Specification includes a Sequence Listing.

(56) References Cited

OTHER PUBLICATIONS

Chuanjing Wu, Rong Jiang Yang, Ji Zhou, Shing Bao, Li Zou, Pinggan Zhang, Yongrong Mao, Jianping Wu, Qimin He, "Production and characterisation of a novel chicken IgY antibody raised against C-terminal peptide from human thymidine kinase 1", Journal of Immunological Methods, 277 (2003), 157-169.

Chen Hong-Xiu, Zhang Xiao-Ying, Chen Chen, Zhao Jian-Le, Han Shui-Zhong, Li Yin-Qian, Liu Xiao-Qiang, "Progress on Chicken Monoclonal Antibody Technology", Progress in Biochemistry and Biophysics, 2010, 37 (4), 358-363.

Edzard Spillner, Ingke Braren, Kerstin Greunke, Henning Seismann, Simon Blank, Dion Du Plessis, "Avian IgY antibodies and their recombinant equivalents in research, diagnostics and therapy", Biologicals, 40 (2012), 313-322.

International Search Report in corresponding PCT Application No. PCT/CN2019/102619, dated Nov. 27, 2019; and Written Opinion of the International Searching Authority in corresponding PCT Application No. PCT/CN2019/102619, dated Nov. 27, 2019.

Genebank, "Accession No. XP_025011258.1, Ig lambda chain V-1 region isoform X37 [Gallus gallus]", Mar. 1, 2022, Genebank, May 17, 2018.

Arakawa, H. et al., "Accession No. BAA10010.1, immunoglobulin heavy chain, partial [Gallus gallus]", Genebank, Jul. 26, 2016.

Kiran Kumar Jagarlamudi et al., "Thymidine kinase 1 as a tumor biomarker: technical advances offer new potential to an old biomarker", Biomarkers in Medicine, 2018, vol. 12, No. 9, pp. 1035-1048.

Kiran Kumar Jagarlamudi et al., "Breast and prostate cancer patients differ significantly in their serum Thymidine kinase 1 (TK1) specific activities compared with those hematological malignancies and blood donors: implications of using serum TK1 as a biomarker", BMC Cancer, 2015, vol. 15, No. 66, pp. 1-12, DOI: 10.1186/s12885-015-1073-8.

First Office Action in counterpart China Application No. 201811026810.9, dated Mar. 17, 2022.

The Second Office Action in counterpart China Application No. 201811026810.9, dated Jun. 24, 2022.

Notification to Grant Patent Right for Invention in counterpart China Application No. 201811026810.9, dated Sep. 15, 2022.

* cited by examiner

DEVELOPMENT OF RECOMBINANT CHICKEN IgY MONOCLONAL ANTIBODY AND scFv ANTIBODIES RAISED AGAINST HUMAN TYMIDINE KINASE 1 EXPRESSED IN MAMMALIAN CELLS AND USE THEREOF

CROSS-REFERENCE TO RELATED APPLICATIONS

This application is a Continuation Application of International Application No. PCT/CN2019/102619, filed on Aug. 26, 2019, which claims priority to Chinese Application No. 201811026810.9, filed on Sep. 4, 2018, the entire disclosure of which is incorporated herein by reference.

This application contains a sequence listing submitted as an ASCII text file, named "Seq-List.txt" and created on May 26, 2021, with 9 kilobytes in size. The material in the above-identified ASCII text file is incorporated herein by reference in its entirety.

TECHNICAL FIELD

The present disclosure relates to the field of bioengineering, specifically to a recombinant chicken IgY monoclonal antibody and a recombinant chicken IgY single-chain variable fragment (scFv) antibodies raised against human thymidine kinase 1, and a preparation method and use thereof, more specifically to a monoclonal antibody, an scFv antibody, an isolated RNA and reverse transcripted into cDNA, a suitable vector, an expression of recombinant antibody in mammalian cells, a method for preparing of monoclonal or scFv antibody, an immunoconjugate, a test strip or a test kit, and a use of a monoclonal antibody, an immunoconjugate and a test strip or a test kit to detect abnormal cell proliferation.

BACKGROUND

Thymidine kinase 1 (TK1) is a special kinase that catalyzes deoxythymidine (dThd) to deoxy-thymidylate phosphate (dTMP). TK1 is a cell cycle dependent enzyme, which mainly exists in the cytoplasm. The replication of chromosomal DNA in mammalian cells is restricted to a certain period in the cell cycle, which is called S phase. The enzymatic activities of many enzymes required during the process of DNA precursor synthesis and DNA replication increase when the cell enters the S phase, and decrease after DNA synthesis is completed. A type of special S-phase enzymes, including TK, thymidylate synthase, ribonucleoside diphosphate reductase, and dihydrofolate reductase, are characterized by being greatly induced to increase. Changes in the activity of this type of enzyme reveals the existence of two distinct regulatory mechanisms: one way to start is to increase the enzyme activity in S phase; the other is to reduce the enzyme activity and return to the level before the S phase. The detection of serum thymidine kinase 1 has important clinical detection significance.

Nowadays, there are not many products for the detection of human thymidine kinase 1 (hTK1), mainly for the detection of thymidine kinase 1 in human cell/tissue using the labeled hTK1 antibodies for immunohistochemistry. The serum TK1 (STK1) concentration detection generally uses human TK1 protein as antigen to prepare anti-hTK1 mono/polyclonal antibodies, but the specificity of antibodies are generally not high specificity. Therefore, the existing hTK1 antibody needs to be improved.

SUMMARY

The present disclosure aims to solve at least one of the technical problems existing in the prior art. To this end, an object of the present disclosure is to provide an scFv antibody or monoclonal antibody. The antibody is an anti-hTK1 IgY scFv antibody or monoclonal antibody, with high affinity, avoiding the non-specific reaction of mammalian IgG and having a smaller molecular weight and easier entry into cells.

It should be noted that the present disclosure is completed based on the following work of the inventors. At present, the sensitivity and specificity of anti-human TK1 mono/poly antibodies prepared from different sources of mammalians are limited in detection or therapeutic applications in clinical serology. Many antibodies are murine anti-human TK1 monoclonal antibodies. Since the genetic homology of human TK1 and mouse TK1 is about 84%, and the amino acid homology is about 87%, respectively, the immune response of mice induced by hTK1 protein is low. Therefore, the affinity of the selected the monoclonal antibody is also low. On the other hand of disadvantage, it found that the heterophil antibody (HA), a human-derived endogenous antibody, can bind to the Fc, or the epitopes on Fab and F(ab)'2 of many mammalian immunoglobulin Ig. The cross-reactions of HA found that mouse monoclonal antibodies are particularly strong. Thus, the disadvantage are considered to be the biggest cause of false positive and false negative and thus limited to use in clinicians. Since the phylogenetic distance between mammals and avian, the advantage of avian's IgYs neither cross-reaction with HA response, neither rheumatoid factors (RF)—a major source of interference in many immunoassays, reacting with the Fc-portion of mammalian IgG. The IgY poly-antibodies can easily be obtained from the egg yolks of immunized chickens and effectively reduce false positive reaction compare to IgG antibodies. Therefore, chicken IgY has demonstrated the advantages of a wide range of applications in detection and therapeutic applications. However, the repeatability of chicken IgY antibodies between batch numbers may sometimes be unstable as compared with monoclonal antibodies, which limits the application in large quantities potentially. The inventors used recombinant antibodies to prepare IgY monoclonal antibodies, and used DNA recombination technology to connect the antibody heavy chain variable region and light chain variable region genes through a short peptide to express the antibody fragment by fusion method. It shows high antigen specificity and affinity of natural antibodies and also no immunoreaction with the Fc segment of mammals, and thus more conducive to being a drug targeting. The small molecular weight ($\approx$30 kDa, antibody is $\approx$150 kDa) is easy to pass through blood vessel wall and solid tumor, which is conducive to the treatment of drugs. The most commonly used expression systems for antibody recombination are *Escherichia coli* expression system and mammalian cell expression system, but each has its own advantages and disadvantages. It is highly expressed in *E. coli* and is easy to prepare in large quantities, but it often forms inclusion bodies with non-biologically active, and the amount of soluble expression is very small, especially when it is difficult to carry out effective modification during translation and expression, which leads to the loss of biological activity, thereby limiting its application. The inventors used a mammalian expression system to express antihTK1 IgY monoclonal antibodies, which not only expressed antibody molecules that specifically bind to hTK1, but also avoided the non-specific immune cross reaction in the Fc fragment of mammalian antibodies, and the monoclonal antibody has high specificity and sensitivity. In addition, the recombinant anti-human TK1 scFv antibody used to detect TK1 molecules in human serum can not only overcome the shortcomings of low affinity and high background caused by cross-reactivity of mouse monoclonal antibodies, but also can improve the easy entry of small molecule antibodies into cells and improve the detection effect in immunohistochemistry.

Thus, according to one aspect of the present disclosure, the present disclosure provides a monoclonal antibody. According to an embodiment of the present disclosure, a light chain of the monoclonal antibody includes an amino acid sequence SEQ ID NO: 1. Specifically, the amino acid sequence SEQ ID NO: 1 may be a light chain variable region sequence, and a heavy chain includes an amino acid sequence SEQ ID NO: 2. Specifically, the amino acid sequence SEQ ID NO: 2 may be a heavy chain variable region sequence.

(SEQ ID NO: 1)
MKSLLPTAAAGLLLLAAQPAMAAVTLDESGGGLQTPGGALSLVCKGSGFT

FSSDAMGWMRQAPGKGLEFVARINSAGSYTDYGSAVDGRATISRDNGQST

VRLQLNNLRAEDTSTYFCAKSPGGFSCAYGLCWDAAGSIDAWGHGTEVIV

S (SEQ ID NO: 2)
ALTQPSSVSANLGGTVKITCSGGANYYGWFQQKTPGSAPVSLIYESTKRP

SNIPSRFSGSKSGSTGTLTITGVRADDEAVYYCGTYDSSTHTTIFGAGTT

LTVLGASGAEFAAPSVFIFPPSDEQLKSGTASVVCLLNNFYPRE

The monoclonal antibody according to the embodiment of the present disclosure is a recombinant anti-hTK1 IgY monoclonal antibody, which has high affinity and low cross-reactivity, effectively avoiding the non-specific reaction of IgG Compared with IgG, the monoclonal antibodies of the present disclosure have a smaller molecular weight and are easier to enter cells, and can improve the detection effect in immunohistochemistry, can easily pass through blood vessel walls and solid tumors, and can be beneficial to the treatment with drugs.

Besides, the monoclonal antibody according to the foregoing embodiment of the present disclosure may also have the following additional technical features.

According to an embodiment of the present disclosure, the monoclonal antibody further includes a linkage peptide including an amino acid sequence SEQ ID NO: 3. Thus, the linkage peptide links C-terminal of the light chain variable region and N-terminal of the heavy chain variable region to form a monoclonal antibody. The linkage peptide has good flexibility and will not affect the correct folding of the variable region of the heavy chain and the variable region of the light chain.

According to an embodiment of the present disclosure, the monoclonal antibody further includes at least one of the following expression elements: a signal peptide including an amino acid sequence SEQ ID NO: 4; and a tag including an amino acid sequence SEQ ID NO: 5. The signal peptide guides the secretion of the recombinant monoclonal antibody to the outside of the cell, which is beneficial to the purification of the recombinant monoclonal antibody. According to an embodiment of the present disclosure, the signal peptide is linked to the N-terminal of the light chain variable region of the monoclonal antibody. The signal peptide in the embodiment of the present disclosure is the mouse IL-2 signal peptide commonly used for recombinant antibody production with CHO expression system. The linkage peptide is used to link the tag sequence to the antibody, and the antibody is separated by the tag sequence. The tag is human influenza virus hemagglutinin 9 peptide. The tag can be linked to the C-terminal of the heavy chain variable region of the monoclonal antibody.

(SEQ ID NO: 3)
SGGGSGGGGSGGGGSGGGS (SEQ ID NO: 4)
MGRMQLLSCIALSLALVTNS (SEQ ID NO: 5)
YPYDVPDYA

According to an embodiment of the present disclosure, the monoclonal antibody includes an amino acid sequence SEQ ID NO: 6.

(SEQ ID NO: 6)
MGRMQLLSCIALSLALVINSMAAVTLDESGGGLQTPGGALSLVCKGSGFT

FSSDAMGWMRQAPGKGLEFVARINSAGSYTDYGSAVDGRATISRDNGQST

VRLQLNNLRAEDTSTYFCAKSPGGFSCAYGLCWDAAGSIDAWGHGTEVIV

SSGGGSGGGGSGGGGSGGGSALTQPSSVSANLGGTVKITCSGGANYYGWF

QQKTPGSAPVSLIYESTKRPSNIPSRFSGSKSGSTGTLTITGVRADDEAV

YYCGTYDSSTHTSIFGAGTTLYPYDVPDYA

According to the second aspect of the present disclosure, the present disclosure provides an scFv antibody. According to an embodiment of the present disclosure, a light chain of the scFv antibody includes the amino acid sequence SEQ ID NO: 1, and a heavy chain includes the amino acid sequence SEQ ID NO: 2.

The term "scFv antibody" used herein is an antibody formed by linking the variable region of the heavy chain of the antibody and the variable region of the light chain of the antibody through a short peptide (linker). Specifically, the scFv antibodies do not have a constant region, but the functions and immunologic effects of single-chain antibodies and monoclonal antibodies in the embodiments of the present disclosure are the same and similar.

According to an embodiment of the present disclosure, the scFv antibody further includes a linkage peptide including an amino acid sequence SEQ ID NO: 3. thus, the linkage peptide links the N-terminal of the light chain variable region and the C-terminal of the heavy chain variable region to form the scFv antibody. The linkage peptide has good flexibility and will not affect the correct folding of the variable region of the heavy chain and the variable region of the light chain.

According to an embodiment of the present disclosure, the scFv antibody further includes at least one of the following expression elements: a signal peptide including an amino acid sequence SEQ ID NO: 4; and a tag including an amino acid sequence SEQ ID NO: 5. The signal peptide guides the secretion of the recombinant monoclonal antibody to the outside of the cell, which is beneficial to the purification of the recombinant scFv antibody. The signal peptide in the embodiment of the present disclosure is the mouse IL-2 signal peptide commonly used for CHO expression system in recombinant antibody production. The linkage peptide is used to link the tag sequence to the antibody, and the antibody is separated by the tag sequence. The tag is human influenza virus hemagglutinin 9 peptide.

According to a third aspect of the present disclosure, the present disclosure provides a nucleic acid. According to an embodiment of the present disclosure, the nucleic acid encodes the aforementioned monoclonal antibody or scFv antibody. The inventor surprisingly found that the anti-hTK1 IgY scFv antibody or monoclonal antibody encoded by the nucleic acid has high affinity and low cross-reactivity, effectively avoiding the non-specific reaction of mammalian IgG Compared with IgG, the relative molecular weight of the scFv antibody or monoclonal antibody is smaller, which makes the scFv antibody or monoclonal antibody easier to enter the cell, thereby improving the detection efficacy in immunohistochemistry, and making it easy to pass through the blood vessel wall and solid tumors, which can be beneficial to the treatment of drugs.

According to an embodiment of the present disclosure, the nucleic acid further includes at least one of the following expression elements:

A KOZAK sequence including a nucleotide sequence SEQ ID NO: 7, which can be combined with the translation initiation factor to mediate the translation initiation of mRNA containing a 5'cap structure.

(SEQ ID NO: 7)
GCCACCATGG

A signal peptide including a nucleotide sequence SEQ ID NO: 8, and the signal peptide guides the secretion of the recombinant scFv antibody to the outside of the cell.

(SEQ ID NO: 8)
ATGCAACTCCTGTCTTGCATTGCACTAAGTCTTGCACTTGTCACAAACAG

TATGGCCGCA

A tag including a nucleotide sequence SEQ ID NO: 9, and the antibody is separated by the tag sequence, the tag is the sequence of the hemagglutinin of the human influenza virus.

(SEQ ID NO: 9)
TACCCATACGACGTCCCAGACTACGCT

According to an embodiment of the present disclosure, the nucleic acid includes a nucleotide sequence SEQ ID NO: 10.

(SEQ ID NO: 10)
AGATCTGCCACCATGGGCAGGATGCAACTCCTGTCTTGCATTGCACTAAG

TCTTGCACTTGTCACAAACAGTATGGCCGCAGTGACGTTGGACGAGTCCG

GGGGCGGCCTGAAGACGCCCGGAGGAGCGCTCAGCCTCGTCTGCAAGGCC

TCCGGGTTCACCTTCAGTTACTATAGCCTGGCCTGGGTGCGACAGGCGCC

CGGCAAGGGGTTGGAGTTCGTTGCTGATATTGACAATAGTGGTAGTAGTT

ACACAACATACGGGCGGCGGTGAAGGGCCGTGCCACCATCTCGAGGGAC

-continued
AACGGGCAGAGCACAGTGAGGCTGCAGCTGAACAACCTCAGGGCTGAGGA

CACCGGCACCTACTACTGCGCCAAAGATGCTCATACTAATAGTTTTATTG

GTGATGATATCGACGGGTGGGGCCACGGGACCGAAGTCATCGTCTCCTCT

GGTGGAGGATCAGGTGGAGGAGGATCCGGAGGTGGTGATTCTGGAGGTGG

TTCTGCGCTGACTCAGCCGTCCTCGATGTCAGCGAACCCGGGAGAAACCG

TCAAGATCACCTGCTCCGGGGGTGGCAGCTACTATGGAAGTTACTATTAT

GGCTGGTACCAGCAGAAGTCTCCTGGCAGTGCCCCTGTCACTGTGATCCA

TAGCAACGACAAGAGACCCTCAGACATCCCTTCACGATTCTCCGGTTCCA

AATCCGGCTCCGCAGCCACATTAACCATCACTGGGGTCCAAGCCGAGGAC

GAGGCTGTCTATTTCTGTGGTGGCTACGACAGCAACAGTGATAGTGCAAT

ATTTGGGGCCGGGACAACCCTGTACCCATACGACGTCCCAGACTACGCTT

AACCGCGG

The AGATCT sequence at the 3'-terminal and the CCGCGG at the 5-terminal are restriction sites.

It should be noted that DNA is transcribed into mRNA, and mRNA is processed by splicing and other processes to translate into protein. The so-called coding sequence is the DNA sequence corresponding to the protein sequence one-to-one. The sequence does not contain other sequences that are not corresponding to the protein, and does not consider sequence changes during the process of mRNA processing, etc. In short, the coding sequence corresponds exactly to the codon of the protein. In other words, the coding sequence is the sequence that encodes a protein product.

In the present disclosure, the nucleic acid further includes a nucleotide sequence in which one or more bases are substituted, deleted, or modified to the nucleotide sequence SEQ ID NO: 10, referring to the substitution, deletion, and addition of no more than 2-60 bases, or no more than 2-40 bases, or no more than 3-30 bases, or no more than 4-15 bases, or no more than 5-10 bases, or no more than 6-8 bases represented by consecutive integers at the 5'-terminal and/or 3'-terminal of the nucleotide sequence separately or simultaneously and/or within the sequence.

In the present disclosure, the nucleic acid further includes a nucleotide sequence in which one or more bases are substituted, deleted, or modified to the nucleotide sequence SEQ ID NO: 10, which has the same or similar anti-HTK1 scFv antibody or monoclonal antibody function with the nucleotide sequence SEQ ID NO: 10.

According to a fourth aspect of the present disclosure, the present disclosure provides a recombinant vector. According to an embodiment of the present disclosure, the recombinant vector includes the aforementioned nucleic acid. After the vector according to the embodiment of the present disclosure is introduced into host cells, it can secrete and produce anti-hTK1 scFv antibody or monoclonal antibody. The scFv antibody or monoclonal antibody has good immunoreactivity, high affinity, low cross-reactivity, and effectively avoids the non-specific reaction of IgG Compared with IgG the scFv antibody or monoclonal antibody has a smaller molecular weight and is easier to enter cells, which can improve the detection efficacy in immunohistochemistry. The scFv antibody or monoclonal antibody is easy to pass through blood vessel walls and solid tumors, which can be beneficial to the treatment of drugs.

The vector can be obtained by, for example, inserting the above-mentioned nucleotide sequence into a cloning vector or expression vector, or can be obtained by artificial synthesis.

According to an embodiment of the present disclosure, the vector of the recombinant vector is a eukaryotic vector, such as pIRES2-EGFP vector. Therefore, it contains the regulatory elements required for expression in mammalian cells, and can secrete and express anti-hTK1 scFv antibody in mammalian cells.

According to a fifth aspect of the present disclosure, the present disclosure constructs a recombinant antibody expression vector in host cells. According to an embodiment of the present disclosure, the host cells contain the aforementioned vector. The recombinant host cells according to the embodiment of the present disclosure can secrete and produce anti-hTK1 scFv antibody or monoclonal antibody. The scFv antibody or monoclonal antibody has good immunoreactivity, high affinity, low cross-reactivity, and effectively avoids the non-specific reaction of IgG Compared with IgG the scFv antibody or monoclonal antibody has a smaller molecular weight and is easier to enter cells, which can improve the detection effect in immunohistochemistry. The scFv antibody or monoclonal antibody is easy to pass through blood vessel walls and solid tumors, which can be beneficial to the treatment of drugs.

According to some embodiments of the present disclosure, the host cells can be obtained by transforming the aforementioned vector into them. The eukaryotic expression vector of the embodiment of the present disclosure is transfected into CHO cells (Chinese hamster ovary cells, which belong to a kind of ovarian fibroblast tour cells), and the obvious expression (green fluorescent protein label) can be observed for 16 hours.

According to a sixth aspect of the present disclosure, the present disclosure provides a method for preparing the aforementioned monoclonal antibody or the aforementioned scFv antibody. According to an embodiment of the present disclosure, the method includes: culturing host cells encoding monoclonal/scFv antibody under conditions suitable for protein expression and secretion, to obtain the monoclonal antibody or scFv antibody. The scFv antibody or monoclonal antibody prepared by the method has good immunoreactivity, high affinity, low cross-reactivity, and effectively avoids the non-specific reaction of IgG Compared with IgG the scFv antibody or monoclonal antibody has a smaller molecular weight and is easier to enter cells, which can improve the detection effect in immunohistochemistry. The scFv antibody or monoclonal antibody is easy to pass through blood vessel walls and solid tumors, which can be beneficial to the treatment of drugs.

According to some embodiments of the present disclosure, the method further includes purifying the scFv antibody or the monoclonal antibody, and the purifying treatment can be performed by affinity chromatography on agarose gel column of hTK1-31 amino acid coupling polypeptide antigen. The scFv antibody or monoclonal antibody obtained by the purification treatment has high purity and activity.

According to a seventh aspect of the present disclosure, the present disclosure provides an immunoconjugate. According to an embodiment of the present disclosure, the immunoconjugate includes: the aforementioned monoclonal antibody, or the aforementioned scFv antibody; and a conjugate moiety selected from the group consisting of drugs, toxins, cytokines, radionuclides or enzymes. According to the immunoconjugate of the embodiment of the present disclosure, by coupling the aforementioned scFv antibody or monoclonal antibody, the drug effect of the conjugate moiety can be effectively improved, and the therapeutic effect on abnormal cell diseases, such as tissue hyperplasia and tumors, is better.

According to an eighth aspect of the present disclosure, the present disclosure provides a test strip or a test kit. According to an embodiment of the present disclosure, the test strip and the test kit contain the aforementioned monoclonal antibody, the aforementioned scFv antibody, the aforementioned immunoconjugate, or their combination with a detectable marker. The test strip or test kit can be used to detect hTK1 to determine the abnormal proliferation of cells. The test strip or the test kit has high detection sensitivity and good specificity.

According to an embodiment of the present disclosure, the detectable marker is selected from: colloidal gold marker, fluorescent marker, isotope marker, enzyme marker, preferably the enzyme marker is HRP enzyme marker.

According to the eighth aspect of the present disclosure, the present disclosure provides a use of the aforementioned monoclonal antibody, the aforementioned scFv antibody, the aforementioned immunoconjugate, and the aforementioned test strip or test kit for detecting abnormal cell proliferation. Therefore, the aforementioned monoclonal antibody or scFv antibody, the aforementioned immunoconjugate, and the aforementioned test strip or test kit can be used to detect hTK1 to determine the abnormal proliferation of cells, with high detection sensitivity and good specificity.

There are many cases of abnormal cell proliferation. For the anti-hTK1 monoclonal antibody or scFv antibody of the embodiment of the present disclosure, the abnormal cell proliferation may include pregnancy, tissue hyperplasia and tour, and the detection sensitivity and accuracy are high.

The additional aspects and advantages of the present disclosure will be partly given in the following description, and part will become obvious from the following description, or be understood through the practice of the present disclosure.

BRIEF DESCRIPTION OF THE DRAWINGS

The above and/or additional aspects and advantages of the present disclosure will become obvious and easy to understand from the description of the embodiments in combination with the following drawings.

DETAILED DESCRIPTION OF THE EMBODIMENTS

The embodiments of the present disclosure are described in detail below, and examples of the embodiments are shown in the accompanying drawings. The same or similar reference numerals indicate the same or similar elements or elements with the same or similar functions. The embodiments described below with reference to the drawings are exemplary, and are only used to explain the present disclosure, but should not be construed as limiting the present disclosure.

The present disclosure will be described below with reference to specific embodiments. It should be noted that these embodiments are merely illustrative and should not be understood as limiting the present disclosure.

The solution of the present disclosure will be explained below in combination with examples. Those skilled in the art will understand that the following embodiments are only used to illustrate the present disclosure and should not be regarded as limiting the scope of the present disclosure. Where specific techniques or conditions are not indicated in the embodiments, the procedures shall be carried out in accordance with the techniques or conditions described in the literature (for example, "Molecular Cloning Experiment Guide" by J. Sam brook et al., translated by Huang Pelting et al., third edition, Science Press) in the field or in accordance with the product specification. The reagents or instruments used without the manufacturer's indication are all conventional products that can be purchased commercially, for example, purchased from Sigma.

Embodiment 1

A method for expressing an anti-hTK1 scFv antibody provided by the embodiment of the present disclosure is as follows:
1. Constructing Mammalian Cell Expression System:
1.1 Designing a Primer According to a regulatory element required for eukaryotic expression and an scFv antibody gene sequence with prokaryotic activity, upstream and downstream primer sequences for amplifying chicken IgY antibody variable region genes from the scFv antibody gene library are designed:
HTK1 SCFVHVFP (SEQ ID NO: 11)
5': GAAGATCTGCCACCATGGGCAGGATGCAACTCCTGTCTTGCATTGC

ACTAAGTCTTGCACTTGTCACAAACAGTGCGCTGACTCAGCCGTCCTC-3'

HTK1 SCFVLVRP (SEQ ID NO: 12)
5': CGGGATCCTTAAGCGTAGTCTGGGACGTCGTATGGGTAAGAGGAGA

CGATGACTTCGG-3'

1.2 Gene Cloning

The phage display system screened the scFv antibody gene with activity against the C-terminal 31 peptide of human molecule hTK1 as a template, and applied a pair of designed primers to amplify the sequence suitable for eukaryotic expression vector construction according to the following procedures. Human thymidine kinase 1 (hTK1) molecular gene is 702 bp in length, encoding 234 amino acids, and the C-terminal 31 peptide is located at positions 195-225aa of the full-length protein molecule.
Amplification System: PCR Reaction System: 10*PCR Buffer

| | |
|---|---|
| dNTP (2.5 μM) | 4 μl |
| HTK1 SCFVHVFP primer (20 μM) | 2 μl |
| HTK1 SCFVLVRP primer (20 μM) | 2 μl |
| scab-pMoPac-hck-SBP plasmid template | 0.5 μl |
| ddH₂O | 36.25 μl |
| Taq enzyme | 0.25 ul |

Amplification Parameters:

| Temperature/ | Time | Note |
|---|---|---|
| 94° C. | 2 min | |
| 94° C. | 45 min | 30 cycle |
| 65° C. | 45 min | |
| 72° C. | 1 min | |
| 72° C. | 5 min | |
| 4° C. | ∞ | |

The amplified sequence contains the restriction sites required for construction, the kozak sequence GCCAC-CATGG required for eukaryotic expression, the N-terminal signal peptide MGRMQLLSCIALSLALVTNS sequence required for animal cells secretion and expression, the linker sequence GGGSGGGGSGGGGSGGGS linking the heavy and light chain variable regions, and the tag sequence for detection and purification (human influenza virus hemagglutinin 9 peptide, YPYDVPDYA sequence).

Figure 1:
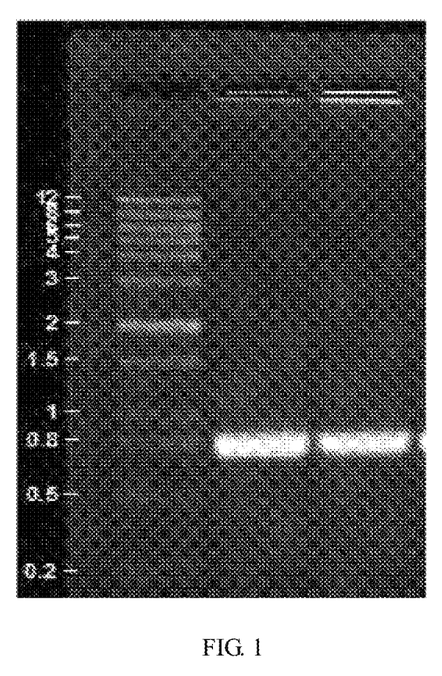
FIG. 1 shows a schematic diagram of a PCR identification result of scFv antibody according to an embodiment of the present disclosure.
Figure 2:
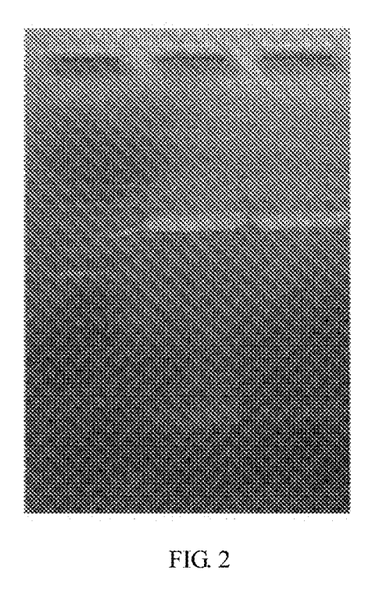
FIG. 2 shows a schematic diagram of a result of double digestion agarose electrophoresis according to an embodiment of the present disclosure.

The PCR amplified product was identified by agarose electrophoresis, and the target fragment was recovered.
1.3 Linking Expression Vector and Target Gene The fragments purified by electrophoresis and the expression vector pIRSE2-EGFP were digested with BglII and SacII respectively. After digestion, the scFv antibody fragments and the linearized vector fragments are recovered by electrophoresis to remove the small fragments and enzyme protein molecules at both ends of the excision. The two recovered fragments are mixed in an equal molar ratio and ligated with T4 ligase to obtain an expression vector ligated with the target gene.
1.3.1 BglII Digestion Pires2-EGFP plasmid 2 ug, scfv gene PCR amplification product 1 ug, 10*NEB Buffer 5 μl, BglII enzyme 1 μl, sterilized deionized water to 50 μl, digestion overnight (14 h) at 37° C., the product is purified and recovered by ethanol/sodium acetate precipitation method.
1.3.2 SacII Digestion The product was recovered by digestion with Bgl II, 10*cutsmart Buffer 5 μl, Sac II enzyme 1 sterilized deionized water to 50 μl, 37° C. for 1 h, and the product was purified and recovered by electrophoresis Qiagen gel recovery kit.
1.3.3 Enzyme Linking and Conversion Take the double digestion product of Pires2-EGFP and the double digestion product of scAB-pMoPac PCR amplification product (vector: the molar ratio of insert fragment is about 1:3). The vector is about 200 ng, 2*enzyme link buffer 10 μl, T4 ligase 1 μl, water to 20 μl, overnight at 16° C., the product was purified and recovered by ethanol/sodium acetate precipitation method (20 μl). Take 1 μl of the recovered product and add 40 μl DH5α competent cells to stand on ice for 2 minutes, add to a pre-cooled 1 mm electroporation cup, 1.8 KV, 5 mm electroporation, immediately add 1 ml SOC medium, incubate at 200 r/min for 1 h, remove and add to the SOB plate containing 50 ug/ml kana resistance, and cultivate overnight at 37° C.
1.4 Identification of Expression Vector Direct heat shock transformation or electrotransformation of the ligation product into DH5α competent cells (Solarbio, C1100). After transformation, spread all the transformed bacteria on an agar plate containing kanamycin and invert it at 37° C. for 16-20 hours. From the bacterial colonies grown on the plate, after overnight at 37° C., pick 5-10 colonies and place them in 5 milliliters of LB medium containing kanamycin for 16 hours to extract plasmids. After purification of the plasmid, double enzyme digestion with BglII and SacII can be used to cut a clone of 800 bp fragment (as shown in FIG. 1), perform sequence determination, and determine the target gene again. The determined sequence was analyzed with DNAMANV6, and the determined sequence was exactly the same as the designed optimized sequence. The transformant was subjected to PCR amplification of scFv antibody gene, and the transformant colony was amplified and cultured, and the plasmid DNA was extracted, and then double-enzyme digestion with BglII and SacII was performed. The results are shown in FIG. 2, and the results show that DNA fragments of the same size can be generated from scFv antibody genes. The plasmid DNA with the correct size is sent to GenScript Biotechnology Company for sequence determination, and the determined sequence is exactly the same as the designed optimized sequence.

2. Transfection of Mammalian Cells CHO

Chinese Hamster Ovary (CHO) cells were isolated from an adult female hamster ovary by Dr. Theodore T. Puck in Colorado in 1957. They are epithelial adherent cells and are a widely used cell line in bioengineering. The cell is immortal and can be passaged for more than one hundred generations. In addition, CHO cells have an advantage in genetic engineering. These cells are fibroblast, which are non-secretory cells, and rarely secrete CHO endogenous proteins, so they are very beneficial for the separation and purification of target proteins. CHO cells can form active dimers with glycosylation function, and are ideal hosts for the expression of complex biological macromolecules. The antibody protein obtained has biological characteristics completely similar to those naturally produced by humans. In this example, the expression vectors for host mammalian cells, such as CHO cells.

2.1 Cell Preparation

Choose a 24-well cell culture plate in each well, pass the CHO cells 24 hours before transfection, the cells will reach 70% to 90% abundance on the day of transfection. When the abundance is 70% to 90%, the suspension cells should be in the logarithmic growth phase during transfection.

2.2 Vector DNA Preparation

After diluting 1 μg of the vector DNA constructed in "Step 1" in 100 μL/well of serum-free DMEM or other serum-free growth medium, mix each 1 μg DNA: 2 μL the transfection agent TurboFect, and the transfection efficiency is high. Vortex to mix well, and add 2 μL/well to the diluted vector DNA.

Transform into Host Cells Instantaneously

Incubate the mixed vector DNA and transfection agent TurboFect at room temperature for 15-20 minutes, and add 100 μL of the transfection reagent/DNA mixture to the culture medium for incubation. During the incubation, do not remove the medium, shake the plate gently to achieve an even distribution of the complex. Incubate in a carbon dioxide incubator at 37° C. to obtain transfected cells.

2.4 Expression Detection 2.4.1 Fluorescence Microscopy

Figure 3:
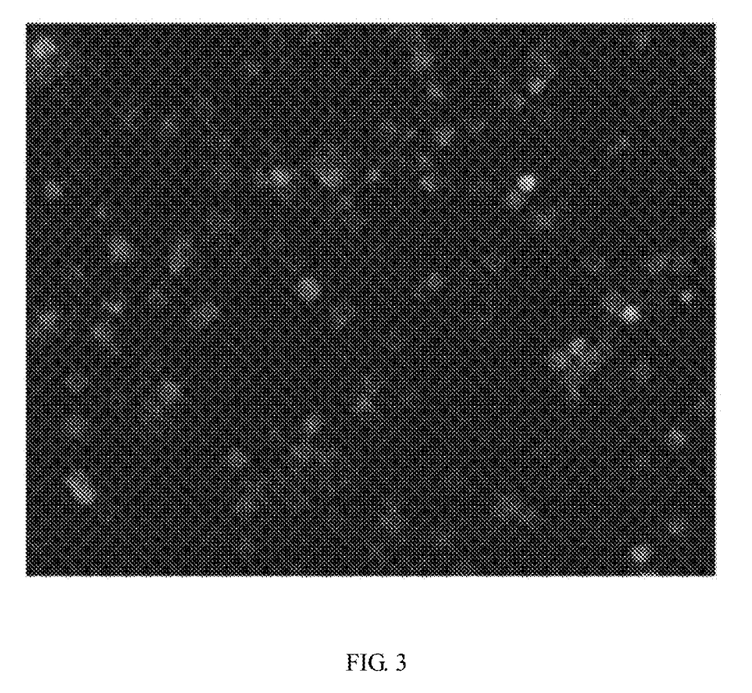
FIG. 3 shows a schematic diagram of fluorescence microscopic observation of CHO cells transfected with scFv antibody gene eukaryotic expression vector according to an embodiment of the present disclosure.

After 48 hours of transfection, by observing the expression of cellular fluorescent protein, the result is shown in FIG. 3, the cells showing green fluorescence accounted for more than 75% of the total number of cells. Since the green fluorescent selective marker protein is in the same expression regulatory sequence as the scFv antibody gene, the various regulatory elements on the surface work normally.

2.4.2 Indirect ELISA Detection

The recombinant IgY scFv antibody contains not only the hypervariable region that binds to hTK1, but also the highly conserved framework region (FR). In this embodiment, the HA 9-peptide tag of human influenza hemagglutinin was added. Therefore, when detecting recombinant single-chain antibodies by indirect ELISA, biotin-labeled anti-full-length IgY secondary antibody and horseradish peroxidase-labeled anti-human influenza hemagglutinin HA 9-peptide monoclonal antibodies were used as labeled antibodies, to detect recombinant anti-hTK1 single-chain antibody expressed in CHO cells. The supernatant of the transfected cells was collected and the expression level of recombinant scFv antibody was detected by ELISA experiment. The specific method is as follows:

(1) Dilute the recombinant hTK1 protein with 1× coating solution to a concentration of 0.5 ug/ml, 100 μl per well, and coat overnight at 4° C.

(2) Wash the ELISA plate once with 400 μl/well of the plate washer, add 200 μl/well of blocking solution, and block at 37° C. for 1 hour.

(3) Wash the ELISA plate once with 400 μl/well of the plate washer, add 100 μl/well of transfected cell supernatant, normal CHO cell blank supernatant and diluted IgY positive control, and react at 37° C. for 1 hour.

(4) Wash the ELISA plate 3 times with 400 μl/well of the plate washer, add 1:20,000 diluted HRP-labeled goat anti-mouse IgG secondary antibody, biotin-labeled anti-full-length IgY secondary antibody and horseradish peroxidase-labeled streptavidin, 100 μl/well.

(5) React at 37° C. for 1 hour. Wash the ELISA plate 3 times with 400 μl/well of the plate washer, and add 100 μl/well of single-component TMB color developing solution VII, and react at 37° C. for 10-15 minutes.

(6) Add stop solution 50 μl/well to stop the reaction, put the ELISA plate into the microplate reader, and measure the absorbance at 450 nm wavelength with 620 nm as the reference wavelength.

| coating antigen | donkey IgG antibody labeled with anti-full-length IgY biotin | | | anti-HA mouse monoclonal antibody labeled with HRP | |
|---|---|---|---|---|---|
| | Transfected CHO supernatant | CHO supernatant | IgY | Transfected CHO supernatant | CHO supernatant |
| HTK1, 50 ng/well | 1.623 | 0.245 | 2.985 | 0.867 | 0.334 |
| coating solution | 0.235 | 0.221 | 0.243 | 0.302 | 0.362 |

The results showed that the donkey IgG antibody labeled with anti-full-length IgY biotin was used as the labeled antibody. The OD value of the CHO cell supernatant transfected with the scFv antibody gene is 6.6 times that of the CHO cell supernatant not transfected, and the ratio of the recombinant hTK1 antigen to the negative antigen control is 6.9. The results of the detection of recombinant scFv antibody detected by the monoclonal antibody against the 9 peptide of HA of human influenza hemagglutinin as the labeled antibody showed that the OD value of the CHO cell supernatant transfected with the scFv antibody gene was 2.6 times that of the untransfected CHO cell supernatant, and the ratio of the recombinant hTK1 antigen to the negative antigen control was 0.287. Therefore, the application of the two label detections proved that the transfected scFv antibody gene showed obvious expression in CHO cells.

In the description of this Specification, description with reference to the terms "an embodiment", "some embodiments", "examples", "specific examples", or "some examples" etc. mean that the specific features, structures, materials or characteristics described in combination with the embodiment or example are included in at least one embodiment or example of the present disclosure. In this Specification, the schematic representations of the above terms do not necessarily refer to the same embodiment or example. Moreover, the described specific features, structures, materials or characteristics may be combined in any one or more embodiments or examples in a suitable manner.

Although the embodiments of the present disclosure have been shown and described, those of ordinary skill in the art can understand various changes, modifications, substitutions and modifications can be made to these embodiments without departing from the principle and purpose of the present disclosure. The scope of the present disclosure is defined by the claims and their equivalents.

What is claimed is:

1. A recombinant chicken IgY scFv antibody raised against human thymidine kinase 1, wherein the scFv antibody comprises a light chain comprising the amino acid sequence of SEQ ID NO: 1, and a heavy chain comprising the amino acid sequence of SEQ ID NO: 2.

2. The recombinant chicken IgY scFv antibody raised against human thymidine kinase 1 of claim 1, wherein the scFv antibody further comprises: a linkage peptide comprising the amino acid sequence of SEQ ID NO: 3.

3. The recombinant chicken IgY scFv antibody raised against human thymidine kinase 1 of claim 1, wherein the scFv antibody further comprises at least one of the following expression elements:

a signal peptide comprising the amino acid sequence of SEQ ID NO: 4; and a tag comprising the amino acid sequence of SEQ ID NO: 5.

4. The recombinant chicken IgY scFv antibody raised against human thymidine kinase 1 of claim 1, wherein the scFv antibody comprises the amino acid sequence of SEQ ID NO: 6.

5. A recombinant chicken IgY monoclonal antibody raised against human thymidine kinase 1, wherein the monoclonal antibody comprises a light chain comprising the amino acid sequence of SEQ ID NO: 1, and a heavy chain comprising the amino acid sequence of SEQ ID NO: 2.

6. The recombinant chicken IgY monoclonal antibody raised against human thymidine kinase 1 of claim 5, wherein the monoclonal antibody further comprises: a linkage peptide comprising the amino acid sequence of SEQ ID NO: 3.

7. The recombinant chicken IgY monoclonal antibody raised against human thymidine kinase 1 of claim 5, wherein the monoclonal antibody further comprises at least one of the following expression elements:

a signal peptide comprising the amino acid sequence of SEQ ID NO: 4; and a tag comprising the amino acid sequence of SEQ ID NO: 5.

8. The recombinant chicken IgY monoclonal antibody raised against human thymidine kinase 1 of claim 5, wherein the monoclonal antibody comprises the amino acid sequence of SEQ ID NO: 6.

9. A nucleic acid, wherein the nucleic acid encodes the scFv antibody of claim 1.

10. The nucleic acid of claim 9, wherein the nucleic acid further comprises at least one of the following expression elements:

a KOZAK sequence comprising the nucleotide sequence of SEQ ID NO: 7;

a signal peptide comprising the nucleotide sequence of SEQ ID NO: 8; and a tag comprising the nucleotide sequence of SEQ ID NO: 9.

11. The nucleic acid of claim 9, wherein the nucleic acid comprises the nucleotide sequence of SEQ ID NO: 10.

12. A vector comprising the nucleic acid of claim 9.

13. The vector of claim 12, wherein the vector is an expression vector encoding recombinant antibody, and the expression vector is pIRES2-EGFP vector.

14. Host expression cells comprising the expression vector of claim 13.

15. An immunoconjugate, comprising:
the scFv antibody of claim 1; and
a conjugate moiety selected from a group consisting of drugs, toxins, cytokines, radionuclides or enzymes.

16. An immunoconjugate, comprising:
the monoclonal antibody of claim 5; and
a conjugate moiety selected from a group consisting of drugs, toxins, cytokines, radionuclides or enzymes.

17. A test strip or test kit, comprising the scFv antibody of claim 1, the monoclonal antibody of claim 5, or the immunoconjugate of claim 15 or 16, or a combination thereof with a detectable marker.

* * * * *

SEQUENCE LISTING

```
<160> NUMBER OF SEQ ID NOS: 12

<210> SEQ ID NO 1
<211> LENGTH: 151
<212> TYPE: PRT
<213> ORGANISM: Artificial
<220> FEATURE:
<223> OTHER INFORMATION: Light chain variable region sequence

<400> SEQUENCE: 1

Met Lys Ser Leu Leu Pro Thr Ala Ala Ala Gly Leu Leu Leu Leu Ala
1               5                   10                  15

Ala Gln Pro Ala Met Ala Ala Val Thr Leu Asp Glu Ser Gly Gly Gly
            20                  25                  30

Leu Gln Thr Pro Gly Gly Ala Leu Ser Leu Val Cys Lys Gly Ser Gly
        35                  40                  45

Phe Thr Phe Ser Ser Asp Ala Met Gly Trp Met Arg Gln Ala Pro Gly
    50                  55                  60

Lys Gly Leu Glu Phe Val Ala Arg Ile Asn Ser Ala Gly Ser Tyr Thr
65                  70                  75                  80

Asp Tyr Gly Ser Ala Val Asp Gly Arg Ala Thr Ile Ser Arg Asp Asn
                85                  90                  95

Gly Gln Ser Thr Val Arg Leu Gln Leu Asn Asn Leu Arg Ala Glu Asp
            100                 105                 110

Thr Ser Thr Tyr Phe Cys Ala Lys Ser Pro Gly Gly Phe Ser Cys Ala
        115                 120                 125

Tyr Gly Leu Cys Trp Asp Ala Ala Gly Ser Ile Asp Ala Trp Gly His
    130                 135                 140

Gly Thr Glu Val Ile Val Ser
145                 150

<210> SEQ ID NO 2
<211> LENGTH: 144
<212> TYPE: PRT
<213> ORGANISM: Artificial
<220> FEATURE:
<223> OTHER INFORMATION: Heavy chain variable region sequence

<400> SEQUENCE: 2

Ala Leu Thr Gln Pro Ser Ser Val Ser Ala Asn Leu Gly Gly Thr Val
1               5                   10                  15

Lys Ile Thr Cys Ser Gly Gly Ala Asn Tyr Tyr Gly Trp Phe Gln Gln
            20                  25                  30
```

```
Lys Thr Pro Gly Ser Ala Pro Val Ser Leu Ile Tyr Glu Ser Thr Lys
        35                  40                  45

Arg Pro Ser Asn Ile Pro Ser Arg Phe Ser Gly Ser Lys Ser Gly Ser
    50                  55                  60

Thr Gly Thr Leu Thr Ile Thr Gly Val Arg Ala Asp Asp Glu Ala Val
65                  70                  75                  80

Tyr Tyr Cys Gly Thr Tyr Asp Ser Ser Thr His Thr Thr Ile Phe Gly
                85                  90                  95

Ala Gly Thr Thr Leu Thr Val Leu Gly Ala Ser Gly Ala Glu Phe Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

<210> SEQ ID NO 3
<211> LENGTH: 19
<212> TYPE: PRT
<213> ORGANISM: Artificial
<220> FEATURE:
<223> OTHER INFORMATION: Linkage peptide

<400> SEQUENCE: 3

Ser Gly Gly Gly Ser Gly Gly Gly Ser Gly Gly Gly Ser Gly Gly Ser
1               5                   10                  15

Gly Gly Ser

<210> SEQ ID NO 4
<211> LENGTH: 20
<212> TYPE: PRT
<213> ORGANISM: Artificial
<220> FEATURE:
<223> OTHER INFORMATION: Signal peptide

<400> SEQUENCE: 4

Met Gly Arg Met Gln Leu Leu Ser Cys Ile Ala Leu Ser Leu Ala Leu
1               5                   10                  15

Val Thr Asn Ser
            20

<210> SEQ ID NO 5
<211> LENGTH: 9
<212> TYPE: PRT
<213> ORGANISM: Artificial
<220> FEATURE:
<223> OTHER INFORMATION: Tag

<400> SEQUENCE: 5

Tyr Pro Tyr Asp Val Pro Asp Tyr Ala
1               5

<210> SEQ ID NO 6
<211> LENGTH: 280
<212> TYPE: PRT
<213> ORGANISM: Artificial
<220> FEATURE:
<223> OTHER INFORMATION: Monoclonal antibody

<400> SEQUENCE: 6

Met Gly Arg Met Gln Leu Leu Ser Cys Ile Ala Leu Ser Leu Ala Leu
1               5                   10                  15
```

```
Val Thr Asn Ser Met Ala Ala Val Thr Leu Asp Glu Ser Gly Gly
             20                  25                  30

Leu Gln Thr Pro Gly Gly Ala Leu Ser Leu Val Cys Lys Gly Ser Gly
         35                  40                  45

Phe Thr Phe Ser Ser Asp Ala Met Gly Trp Met Arg Gln Ala Pro Gly
     50                  55                  60

Lys Gly Leu Glu Phe Val Ala Arg Ile Asn Ser Ala Gly Ser Tyr Thr
65                  70                  75                  80

Asp Tyr Gly Ser Ala Val Asp Gly Arg Ala Thr Ile Ser Arg Asp Asn
                 85                  90                  95

Gly Gln Ser Thr Val Arg Leu Gln Leu Asn Asn Leu Arg Ala Glu Asp
            100                 105                 110

Thr Ser Thr Tyr Phe Cys Ala Lys Ser Pro Gly Gly Phe Ser Cys Ala
        115                 120                 125

Tyr Gly Leu Cys Trp Asp Ala Ala Gly Ser Ile Asp Ala Trp Gly His
    130                 135                 140

Gly Thr Glu Val Ile Val Ser Ser Gly Gly Ser Gly Gly Gly Gly
145                 150                 155                 160

Ser Gly Gly Gly Gly Ser Gly Gly Ser Ala Leu Thr Gln Pro Ser
                165                 170                 175

Ser Val Ser Ala Asn Leu Gly Gly Thr Val Lys Ile Thr Cys Ser Gly
            180                 185                 190

Gly Ala Asn Tyr Tyr Gly Trp Phe Gln Gln Lys Thr Pro Gly Ser Ala
        195                 200                 205

Pro Val Ser Leu Ile Tyr Glu Ser Thr Lys Arg Pro Ser Asn Ile Pro
    210                 215                 220

Ser Arg Phe Ser Gly Ser Lys Ser Gly Ser Thr Gly Thr Leu Thr Ile
225                 230                 235                 240

Thr Gly Val Arg Ala Asp Asp Glu Ala Val Tyr Tyr Cys Gly Thr Tyr
                245                 250                 255

Asp Ser Ser Thr His Thr Ser Ile Phe Gly Ala Gly Thr Thr Leu Tyr
            260                 265                 270

Pro Tyr Asp Val Pro Asp Tyr Ala
        275                 280

<210> SEQ ID NO 7
<211> LENGTH: 10
<212> TYPE: DNA
<213> ORGANISM: Artificial
<220> FEATURE:
<223> OTHER INFORMATION: KOZAK sequence

<400> SEQUENCE: 7
gccaccatgg                                                          10

<210> SEQ ID NO 8
<211> LENGTH: 60
<212> TYPE: DNA
<213> ORGANISM: Artificial
<220> FEATURE:
<223> OTHER INFORMATION: Signal peptide

<400> SEQUENCE: 8
atgcaactcc tgtcttgcat tgcactaagt cttgcacttg tcacaaacag tatggccgca   60

<210> SEQ ID NO 9
<211> LENGTH: 27
<212> TYPE: DNA
```

<210> SEQ ID NO 9
<211> LENGTH: 27 (implied)
<212> TYPE: DNA
<213> ORGANISM: Artificial
<220> FEATURE:
<223> OTHER INFORMATION: Tag

<400> SEQUENCE: 9

```
tacccatacg acgtcccaga ctacgct                                          27
```

<210> SEQ ID NO 10
<211> LENGTH: 858
<212> TYPE: DNA
<213> ORGANISM: Artificial
<220> FEATURE:
<223> OTHER INFORMATION: Synthesized Sequence

<400> SEQUENCE: 10

```
agatctgcca ccatgggcag gatgcaactc ctgtcttgca ttgcactaag tcttgcactt      60
gtcacaaaca gtatggccgc agtgacgttg gacgagtccg ggggcggcct gaagacgccc     120
ggaggagcgc tcagcctcgt ctgcaaggcc tccgggttca ccttcagtta ctatagcctg     180
gcctgggtgc gacaggcgcc cggcaagggg ttggagttcg ttgctgatat tgacaatagt     240
ggtagtagtt acacaacata cggggcggcg gtgaagggcc gtgccaccat ctcgagggac     300
aacgggcaga gcacagtgag gctgcagctg aacaacctca gggctgagga caccggcacc     360
tactactgcg ccaaagatgc tcatactaat agtttattg gtgatgatat cgacgggtgg     420
ggccacggga ccgaagtcat cgtctcctct ggtggaggat caggtggagg aggatccgga     480
ggtggtgatt ctggaggtgg ttctgcgctg actcagccgt cctcgatgtc agcgaacccg     540
ggagaaaccg tcaagatcac ctgctccggg ggtggcagct actatggaag ttactattat     600
ggctggtacc agcagaagtc tcctggcagt gcccctgtca ctgtgatcca tagcaacgac     660
aagagaccct cagacatccc ttcacgattc tccggttcca aatccggctc cgcagccaca     720
ttaaccatca ctggggtcca agccgaggac gaggctgtct atttctgtgg tggctacgac     780
agcaacagtg atagtgcaat atttggggcc gggacaaccc tgtacccata cgacgtccca     840
gactacgctt aaccgcgg                                                  858
```

<210> SEQ ID NO 11
<211> LENGTH: 94
<212> TYPE: DNA
<213> ORGANISM: Artificial
<220> FEATURE:
<223> OTHER INFORMATION: Primer

<400> SEQUENCE: 11

```
gaagatctgc caccatgggc aggatgcaac tcctgtcttg cattgcacta agtcttgcac      60
ttgtcacaaa cagtgcgctg actcagccgt cctc                                  94
```

<210> SEQ ID NO 12
<211> LENGTH: 58
<212> TYPE: DNA
<213> ORGANISM: Artificial
<220> FEATURE:
<223> OTHER INFORMATION: Primer

<400> SEQUENCE: 12

```
cgggatcctt aagcgtagtc tgggacgtcg tatgggtaag aggagacgat gacttcgg        58
```